US011612554B2

United States Patent
Botto et al.

(10) Patent No.: US 11,612,554 B2
(45) Date of Patent: Mar. 28, 2023

(54) HAIR TREATMENT COMPOSITIONS CONTAINING AMINO ACIDS

(71) Applicant: L'Oreal, Paris (FR)

(72) Inventors: Anna Botto, Cranford, NJ (US); Liliana Xavier, Mountainside, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/944,965

(22) Filed: Jul. 31, 2020

(65) Prior Publication Data

US 2022/0031591 A1    Feb. 3, 2022

(51) Int. Cl.
| | | |
|---|---|---|
| *A61K 8/44* | (2006.01) | |
| *A61K 8/891* | (2006.01) | |
| *A61K 8/898* | (2006.01) | |
| *A61K 8/86* | (2006.01) | |
| *A61K 8/34* | (2006.01) | |
| *A61K 8/06* | (2006.01) | |
| *A61Q 5/12* | (2006.01) | |
| *A61K 8/36* | (2006.01) | |

(52) U.S. Cl.
CPC .............. *A61K 8/44* (2013.01); *A61K 8/06* (2013.01); *A61K 8/342* (2013.01); *A61K 8/361* (2013.01); *A61K 8/86* (2013.01); *A61K 8/891* (2013.01); *A61K 8/898* (2013.01); *A61Q 5/12* (2013.01); *A61K 2800/5422* (2013.01); *A61K 2800/59* (2013.01); *A61K 2800/87* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 4,137,180 A | 1/1979 | Naik et al. | |
| 4,185,087 A | 1/1980 | Morlino | |
| 4,874,554 A | 10/1989 | Lange et al. | |
| 6,432,420 B2 * | 8/2002 | Ellis | A61K 8/86 424/401 |
| 2009/0263342 A1 * | 10/2009 | Glenn, Jr. | A61K 8/8129 424/70.11 |
| 2010/0203000 A1 * | 8/2010 | Nguyen | A61K 8/86 424/70.17 |

FOREIGN PATENT DOCUMENTS

| | | |
|---|---|---|
| EP | 0530974 A1 | 3/1993 |
| JP | 2007-070469 A | 3/2007 |

OTHER PUBLICATIONS

Amino acids (Jun. 15, 2012).*
Oshimura et al. (J. Cosmetic Science (2007); 58(4): 347-57 (Abstract only).*
Mintel: "Restorative Hair Masque," Pureology Research, XP055804259, Database accession No. 1140611, Jul. 8, 2009.
Mintel: "Shampoo," Natus Brasiliensis Cosmética, XP055804252, Database accession No. 6775009, Aug. 9, 2019.
Mintel: "Extra Shine Salt-Free Shampoo," Niely, XP055804254, Database accession No. 1469591, Jan. 27, 2011.
Mintel: "Conditioner," LG Household & Health Care, XP055804261, Database accession No. 5084061, Sep. 12, 2017.
"L'Oreal Finalizes the Acquisition of Niely Cosmeticos Group in Brazil," XP055804256, May 31, 2015, https://www.loreal-finance.com/system/files/publication-content/documents/LOREAL_Niely_2015_03_31_EN.pdf [retrieved May 13, 2021].
International Search Report and Written Opinion for counterpart French Application No. FR2008766, dated May 13, 2021.
International Search Report and Written Opinion for PCT/US2021/042720, dated Nov. 10, 2021.

* cited by examiner

*Primary Examiner* — Shirley V Gembeh
(74) *Attorney, Agent, or Firm* — The Marbury Law Group, PLLC

(57) ABSTRACT

The disclosure relates to compositions comprising (a) at least one negatively charged amino acid and a derivative thereof, (b) at least one positively charged amino acid and a derivative thereof, (c) at least one silicone copolymer, and (d) at least one emulsifier. The disclosure also relates to packaging systems and kits comprising the compositions, and methods of using the compositions.

18 Claims, No Drawings

HAIR TREATMENT COMPOSITIONS CONTAINING AMINO ACIDS

TECHNICAL FIELD

The present disclosure relates to compositions comprising amino acids for treating and/or caring for keratin fibers, as well as packaging systems and kits comprising the compositions, and methods of using the compositions.

BACKGROUND

Consumers desire strong, healthy hair. However, hair may be weakened or damaged due to certain environmental factors, as well as mechanical or chemical treatments. For instance, exposure to ultraviolet (UV) light from the sun may weaken hair structure, resulting in hair breakage and loss. Likewise, repeated combing, brushing, blow drying, heating, bleaching, dyeing, straightening/waving, and the like may cause damage to hair. Once hair is damaged, it is more prone to further damage and breakage. As such, there is a need for products that can nourish and strengthen hair in order to combat hair damage, deliver repair benefits to damaged hair, and impart overall healthy properties to hair.

Certain active ingredients, such as proteins, peptides, and amino acids, have been employed in hair treatment products. However, there are challenges in developing suitable formulations using such active ingredients for hair treatment or care. For example, when used as ingredients in hair treatment formulations, amino acids may deliver an undesirable feel to the hair, such as lack of flexibility, resulting in rigid and stiff hair. In addition, although it may be beneficial to include increased amounts of amino acids to the compositions, doing so may result in unstable formulations. Thus, there remains a need for hair treatment compositions that can address hair damage.

It has now surprisingly been found that, by using a synergistic combination of ingredients, a hair treatment composition comprising high levels of amino acids can be prepared, which composition is not only stable but which also provides benefits such as, for example, stronger hair that does not feel rigid, and soft, healthy-looking hair that is not weighted down.

SUMMARY

The disclosure relates to compositions useful for treating keratin fibers such as hair, as well as packaging systems and kits containing the compositions, and methods of using the compositions. In various embodiments, the compositions may be used for nourishing and revitalizing damaged hair, preventing or mitigating damage to hair, or maintaining hair health. In various embodiments, the compositions may be used before, after, or during other hair treatments, and be rinsed off or left on the hair.

In one exemplary and non-limiting embodiment, the disclosure relates to a composition for treating or caring for keratin fibers, the composition comprising (a) at least one negatively charged amino acid or a derivative thereof, (b) at least one positively charged amino acid or a derivative thereof, (c) at least one silicone copolymer, (d) at least one nonionic emulsifier, wherein the composition is in the form of an emulsion. In various embodiments, the at least one negatively charged amino acid or derivative thereof may be chosen from glutamic acid, aspartic acid, derivatives thereof, or mixtures thereof, and the at least one positively charged amino acid or derivative thereof is chosen from arginine, lysine, histidine, ornithine, derivatives thereof, or mixtures thereof. In further embodiments, the at least one silicone copolymer is chosen from dimethicone, dimethicone copolymers, amino functional silicones, or mixtures thereof, and in still further embodiments, the at least one nonionic emulsifier is chosen from polysorbates.

In various embodiments, the at least one negatively charged amino acid or derivative thereof and/or the at least one positively charged amino acid or derivative thereof may be present in an amount ranging from about 0.1% to about 10% by weight, relative to the total weight of the composition, and in particular from about 1% to about 5% by weight, relative to the total weight of the composition. In further embodiments, the at least one silicone copolymer may be present in an amount ranging from about 0.1% to about 10% by weight, relative to the total weight of the composition, and in particular from about 1% to about 5% by weight, relative to the total weight of the composition. In still further embodiments, the at least one nonionic emulsifier is present in an amount ranging from about 0.01% to about 5% by weight, relative to the total weight of the composition, and in particular from about 0.1% to about 0.5% by weight, relative to the total weight of the composition.

In a further exemplary and non-limiting embodiment, the disclosure relates to a composition for treating or caring for keratin fibers, the composition being in the form of an emulsion and comprising (a) about 1% to about 3% of at least one negatively charged amino acid, (b) about 1% to about 3% of at least one positively charged amino acid or a derivative thereof, (c) about 1% to about 3% of at least one silicone copolymer, and (d) about 0.1% to about 0.5% of at least one nonionic emulsifier, all weights being by weight relative to the total weight of the composition. In a further embodiment, the at least one negatively charged amino acid or derivative thereof is chosen from glutamic acid, aspartic acid, derivatives thereof, or mixtures thereof; the at least one positively charged amino acid or derivative thereof is chosen from arginine, lysine, histidine, ornithine, derivatives thereof, or mixtures thereof; the at least one silicone copolymer is chosen from dimethicone, dimethicone copolymers, amino functional silicones, or mixtures thereof; and the at least one nonionic emulsifier is chosen from polysorbates.

In yet another exemplary and non-limiting embodiment, the disclosure relates to methods of treating or caring for keratin fibers comprising apply to the keratin fibers a composition comprising (a) at least one negatively charged amino acid or a derivative thereof, (b) at least one positively charged amino acid or a derivative thereof, (c) at least one silicone copolymer, (d) at least one nonionic emulsifier, wherein the composition is in the form of an emulsion. In various embodiments, the at least one negatively charged amino acid or derivative thereof may be chosen from glutamic acid, aspartic acid, derivatives thereof, or mixtures thereof, and the at least one positively charged amino acid or derivative thereof is chosen from arginine, lysine, histidine, ornithine, derivatives thereof, or mixtures thereof. In further embodiments, the at least one silicone copolymer is chosen from dimethicone, dimethicone copolymers, amino functional silicones, or mixtures thereof, and in still further embodiments, the at least one nonionic emulsifier is chosen from polysorbates. In various embodiments, the composition may optionally be rinsed from the hair after an optional leave-in period of time.

In yet another exemplary and non-limiting embodiment, the disclosure relates to a packaging system comprising a container containing a composition for treating or caring for keratin fibers, the composition being in the form of an emulsion and comprising (a) at least one negatively charged amino acid or a derivative thereof, (b) at least one positively charged amino acid or a derivative thereof, (c) at least one silicone copolymer, (d) at least one nonionic emulsifier. In various embodiments, the at least one negatively charged amino acid or derivative thereof may be chosen from glutamic acid, aspartic acid, derivatives thereof, or mixtures thereof, and the at least one positively charged amino acid or derivative thereof is chosen from arginine, lysine, histidine, ornithine, derivatives thereof, or mixtures thereof. In further embodiments, the at least one silicone copolymer is chosen from dimethicone, dimethicone copolymers, amino functional silicones, or mixtures thereof, and in still further embodiments, the at least one nonionic emulsifier is chosen from polysorbates. In various embodiments, the container is chosen from an ampoule, a syringe, a tube, a packet, a pouch, or a bottle.

In yet another exemplary and non-limiting embodiment, the disclosure relates to a kit comprising a first container containing composition for treating or caring for keratin fibers, the composition being in the form of an emulsion and comprising (a) at least one negatively charged amino acid or a derivative thereof, (b) at least one positively charged amino acid or a derivative thereof, (c) at least one silicone copolymer, (d) at least one nonionic emulsifier. In various embodiments, the at least one negatively charged amino acid or derivative thereof may be chosen from glutamic acid, aspartic acid, derivatives thereof, or mixtures thereof, and the at least one positively charged amino acid or derivative thereof is chosen from arginine, lysine, histidine, ornithine, derivatives thereof, or mixtures thereof. In further embodiments, the at least one silicone copolymer is chosen from dimethicone, dimethicone copolymers, amino functional silicones, or mixtures thereof, and in still further embodiments, the at least one nonionic emulsifier is chosen from polysorbates. In various embodiments, the first container is chosen from an ampoule, a syringe, a tube, a packet, a pouch, or a bottle. In further embodiments, the kit comprises at least one second container, optionally containing a composition not according to the disclosure. In still further embodiments, the kit comprises at least one second container configured to apply the composition contained in the first container to keratin fibers.

DESCRIPTION

The present disclosure relates to compositions for treating keratin fibers, the compositions comprising high levels of amino acids, as well as packaging system and kits comprising the compositions, and methods of using the compositions.

I. Compositions

In various exemplary and non-limiting embodiments, compositions according to the present disclosure comprise (a) at least one negatively charged amino acid or a derivative thereof, (b) at least one positively charged amino acid or a derivative thereof, (c) at least one silicone copolymer, and (d) at least one emulsifier. Optionally, the compositions may further comprises (e) at least one solid fatty compound and/or at least one cationic conditioning agent.

Compositions according to the disclosure may provide benefits to the hair such as, for example, strengthening and bonding properties, improved smoothness, frizz control, flexibility, good end seal, strength, compact feel, manageability, overall soft end feel, and/or a healthy appearance.

Amino Acids and Derivatives

Compositions according to the disclosure comprise at least two amino acids. Amino acids are simple organic compounds containing both a carboxylic acid group (—COOH) and an amino group (—NH$_2$), along with a side chain (R group) specific to each amino acid.

Amino acids may be classified as either neutral, anionic, or cationic amino acids based on the charge of the variable side chain. A negatively charged amino acid, i.e., an anionic amino acid, is an amino acid having a net negative charge at neutral pH, and includes amino acids that have been modified to have a net negative charge. A positively charged amino acid, i.e., a cationic amino acid, is an amino acid having a net positive charge at neutral pH, and includes amino acids that have been modified to have a net positive charge. Non-limiting examples of useful acidic amino acids according to the disclosure include aspartic acid, glutamic acid, or the like, neutral amino acids such as glycine, alanine, serine, threonine, methionine, cysteine, valine, leucine, isoleucine, phenylalanine, tyrosine, proline, hydroxyproline, tryptophan, asparagine, glutamine, taurine, creatine, or the like, and basic amino acids such as arginine, lysine, histidine, ornithine, or the like.

In certain embodiments, the composition comprises at least one negatively charged amino acid and at least one positively charged amino acid. In one exemplary and non-limiting embodiment, compositions according to the disclosure comprise at least one negatively charged amino acid chosen from glutamic acid, and at least one positively charged amino acid chosen from arginine.

In further embodiments, derivatives, analogues, and/or steroisomeric configurations of amino acids may be chosen. The amino acids, derivatives, and analogues thereof may be synthetic or natural, modified or unmodified, salts thereof, or the like. Derivatives may include, for example, acyl or ester derivatives, salts thereof, or hydrosalts thereof. A hydrosalt may be hydrohalide, such as chyrochloride derivative.

In various embodiments, derivatives of the amino acids in the compositions are acyl derivatives and/or ester derivatives, resulting from reaction at an amino group, carboxy group, side-chain functional group, or from the replacement of any hydrogen by a heteroatom. For example, in some embodiments, derivatives of the amino acids in the compositions according to the present disclosure may be acyl derivatives or ester derivatives, which have the amino groups (—NH$_2$) of corresponding amino acids modified by acyl groups or ester groups. In some embodiments, an acyl derivative may be an N-alkanoyl derivative in which the alkanoyl moiety has an alkyl chain length of from 3 to 20 carbon atoms, for example, N-butanoyl, N-hexanoyl, N-ocytanoyl, N-alkyl, etc. An acyl derivative may also be a COO-alkyl derivative in which the alkyl group is straight chain and from 1 to 20 carbon atoms, for example, methyl, ethyl, n-propyl, etc. Further, derivatives such as those including hydroxyl groups, e.g. 3-hydroxyproline or 5-hydroxylysine, may be used.

In various embodiments, compositions according to the disclosure include a neutral amino acid or derivative thereof. In further embodiments, compositions according to the disclosure do not include any neutral amino acid or derivative thereof.

In some other embodiments, compositions according to the disclosure are substantially free of amino acids other than negatively-charged and positively-charged amino acids and derivatives thereof. Thus, in some embodiments, the amino acids present in the composition may consist of, or consist essentially of (a) at least one negatively charged amino acid or a derivative thereof, and (b) at least one positively charged amino acid or a derivative thereof.

In various exemplary embodiments, the at least one negatively charged amino acid and/or a derivative thereof, and the at least one positively charged amino acid and/or a derivative thereof, may independently be present in an amount of about 0.1% or more, such as about 0.5% or more, about 1% or more, about 1.5% or more, or about 2% or more by weight, based on the total weight of the composition. In further exemplary embodiments, the at least one negatively charged amino acid and/or a derivative thereof, and the at least one positively charged amino acid and/or a derivative thereof, may independently be present in an amount up to about 10%, such as up to about 5% or more, or up to about 3% by weight, based on the total weight of the composition.

For example, the at least one negatively charged amino acid and/or a derivative thereof, and the at least one positively charged amino acid and/or a derivative thereof, may independently be included in compositions according to the disclosure in amounts ranging from about 0.1% to about 10%, including all subranges therebetween, such as from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 1.5% to about 10%, from about 1.5% to about 9%, from about 1.5% to about 8%, from about 1.5% to about 7%, from about 1.5% to about 6%, from about 1.5% to about 5%, from about 1.5% to about 4%, from about 1.5% to about 3%, from about 1.5% to about 2%, from about 2% to about 10%, from about 2% to about 9%, from about 2% to about 8%, from about 2% to about 7%, from about 2% to about 6%, from about 2% to about 5%, from about 2% to about 4%, or from about 2% to about 3% by weight, relative to the total weight of the composition.

The ratio of the amount of the at least one negatively charged amino acid to the amount of at least one positively charged amino acid may range from about 1:10 to about 10:1. For example, the ratio of the amounts of the at least one negatively charged amino acid to the at least one positively charged amino acid, or the at least one positively charged amino acid to the at least one negatively charged amino acid, may be about 1:10, about 1:9, about 1:8, about 1:7, about 1:6, about 1:5, about 1:4, about 1:3, about 1:2, or about 1:1. In a preferred embodiment, the total amount of the negatively charged amino acids and the total amount of the positively charged amino acids is approximately the same, i.e. present in the composition in a ratio of about 1:1.

Silicone Copolymers

Compositions according to the disclosure comprise at least one silicone copolymer. Without intending to be limited by theory, the at least one silicone copolymer may balance the strengthening properties exhibited by the amino acids and provide benefits such as flexibility, manageability, discipline, an overall softer end feel, etc., as well as improve the stability of the emulsion.

The at least one silicone compound may be chosen from dimethicone, dimethicone copolymers, amino functional silicones, and mixtures thereof. In an embodiment, the at least one silicone compound of the present disclosure is an amino functional silicone.

In an embodiment, the at least one silicone compound of the present disclosure is amino functional silicone comprising at least one functionalized amodimethicone. The term "amino functional silicone" as used herein can mean any silicone comprising at least one primary, secondary or tertiary amine or a quaternary ammonium group (i.e., a quaternized group).

Non-limiting examples of amino functional silicone that may be used include:

a) polysiloxanes corresponding to formula (A):

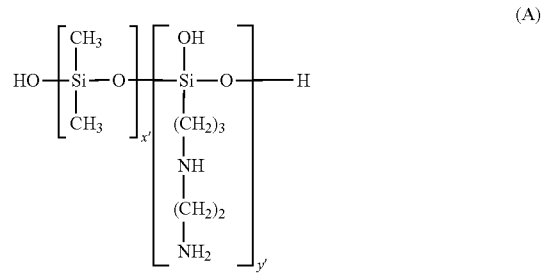

wherein x' and y' are integers such that the weight-average molecular weight (Mw) is comprised between about 5000 and 500000;

b) amino silicones corresponding to formula (B):

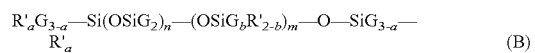

wherein:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and R', which may be identical or different, denote a monovalent radical having formula —$C_qH_{2q}L$, in which q is a number ranging from 2 to 8 and L is an optionally quaternized amino group chosen from the following groups:

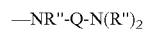

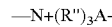

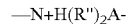

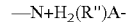

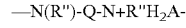

in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A-represents a cosmetically acceptable ion, in particular a halide such as fluoride, chloride, bromide or iodide.

A group of amino silicones corresponding to formula (B) is represented by the silicones called "trimethylsilylamodimethicone" having formula (C):

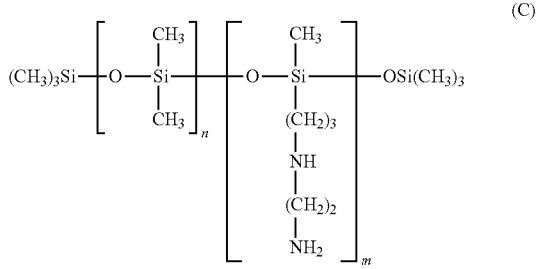
(C)

in which n and m have the meanings as in formula B.

Another group of amino silicones corresponding to formula (B) is represented by silicones of formula (D):

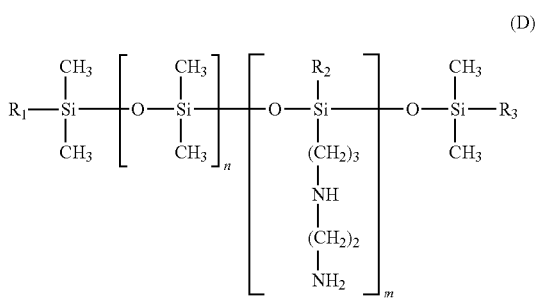
(D)

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5; and R1, R2, R3, which may be identical or different, represent a hydroxy or C1-C4 alkoxy radical, where at least one of the radicals R1 to R3 denotes an alkoxy radical.

In one embodiment, the alkoxy radical is preferably a methoxy radical. In further embodiments, the hydroxy/alkoxy mole ratio ranges preferably from 0.2:1 to 0.4:1 and preferably from 0.25:1 to 0.35:1 and more particularly equals 0.3:1. In various embodiments, the weight-average molecular weight (Mw) of the silicone ranges from 2000 to 1,000,000, such as from 3500 to 200,000.

Another group of amino silicones corresponding to formula (B) is represented by silicones of formula (E):

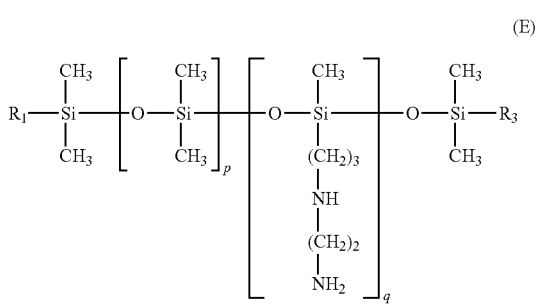
(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5; and $R_1$, $R_2$, which are different, represent a hydroxy or $C_1$-$C_4$alkoxy radical, where at least one of the radicals $R_1$ or $R_2$ denotes an alkoxy radical.

In one embodiment, the alkoxy radical is preferably a methoxy radical. In further embodiments, the hydroxy/alkoxy mole ratio ranges generally from 1:0.8 to 1:1.1 and preferably from 1:0.9 to 1:1 and more particularly equals 1:0.95. In various embodiments, the weight-average molecular weight (Mw) of the silicone ranges preferably from 2000 to 200,000, even more particularly 5000 to 100,000 and more particularly from 10,000 to 50,000.

Commercial products corresponding to these silicones having structure (D) or (E) may include in their composition one or more other amino silicones whose structure is different than formulae (D) or (E). For example, a product containing amino silicones having structure (D) is sold by Wacker under the name Belsil® ADM 652, and products containing amino silicones having structure (E) include those sold by Wacker under the names Fluid WR 1300® or Finish CT 96 E® or SLM 28020®.

Another group of amino silicones corresponding to formula (B) is represented by the following formula (F):

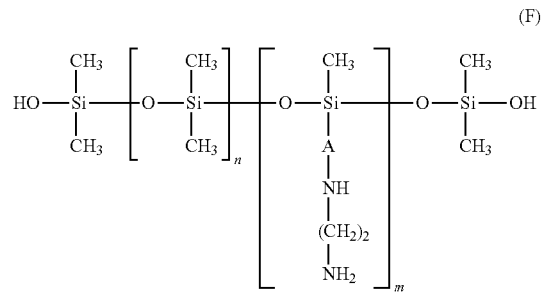
(F)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1,000,000 and even more particularly from 3500 to 200,000. A preferred silicone of formula (F) is amodimethicone (INCI name) sold under the tradename XIAMETER® MEM-8299 Cationic Emulsion by Dow Corning or sold under the tradename SILSOFT 253, by Momentive Performance Materials.

Another group of amino silicones corresponding to formula (B) is represented by the following formula (G):

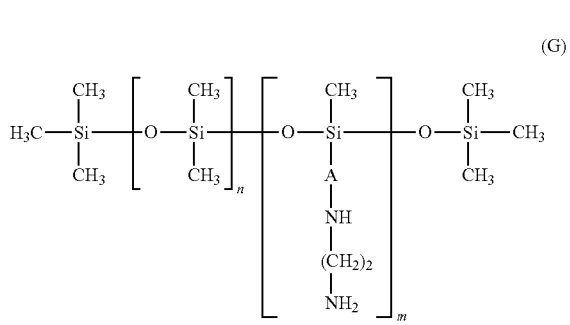

(G)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1,000,000 and even more particularly from 1000 to 200,000. commercially available silicone having this formula is DC2-8566 Amino Fluid by Dow Corning.

c) amino silicones corresponding to formula (H):

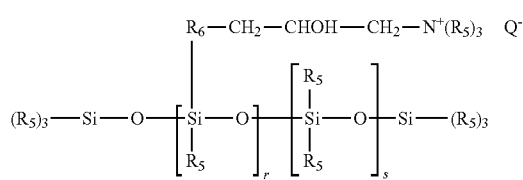

(H)

in which:

R5 represents a monovalent hydrocarbon-based radical containing from 1 to 18 carbon atoms, and in particular a $C_1$-$C_{18}$ alkyl or $C_2$-$C_{18}$ alkenyl radical, for example methyl;

R6 represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q— is an anion such as a halide ion, in particular chloride, or an organic acid salt (for example acetate);

r represents a mean statistical value from 2 to 20 and in particular from 2 to 8; and s represents a mean statistical value from 20 to 200 and in particular from 20 to 50.

Examples of such amino silicones are described in U.S. Pat. No. 4,185,087.

d) quaternary ammonium silicones having formula (I):

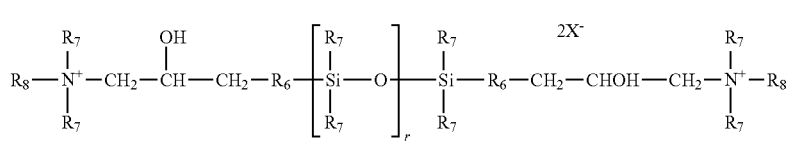

(I)

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

R6 represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X$^-$ is an anion such as a halide ion, in particular chloride, or an organic acid salt (for example acetate); and r represents a mean statistical value from 2 to 200 and in particular from 5 to 100.

Examples of such silicones are described, for example, in patent application EP-A 0530974.

e) amino silicones having formula (J):

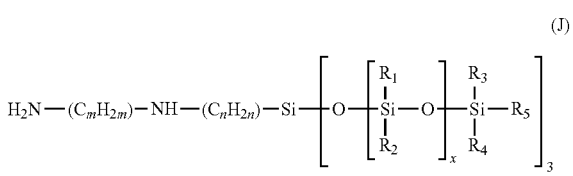

(J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5; and x is chosen such that the amine number is between 0.01 and 1 meq/g.

f) multiblockpolyoxyalkylenated amino silicones, of type (AB)n, A being a polysiloxane block and B being a polyoxyalkylenated block containing at least one amine group. In various embodiments, such silicones may comprise repeating units having one of the following general formulae:

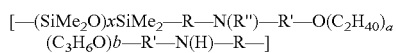

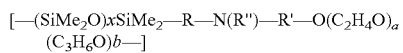

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10000, more particularly from 10 to 5000;

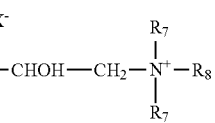

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical; and R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent from 50-95 mol % of the total weight of the silicone, more particularly from 70-85 mol %. The amine content is preferably from 0.02 to 0.5 meq/g of copolymer in a 30% solution in dipropylene glycol, more particularly from 0.05 to 0.2. The weight-average molecular weight (Mw) of the silicone is preferably comprised between 5000 and 1,000,000, more particularly between 10,000 and 200,000. Non-limiting examples include bis-amino PEG/PPG-41/3 aminoethyl PG-propyl dimethicone and PEG-40/PPG-8 methylaminopropyl hydroxypropyl dimethicone copolymer. Commercially available products include the silicones sold under the names SILSOFT A-843 or SILSOFT A+ by Momentive.

g) the alkylamino silicones corresponding to formula (K) below:

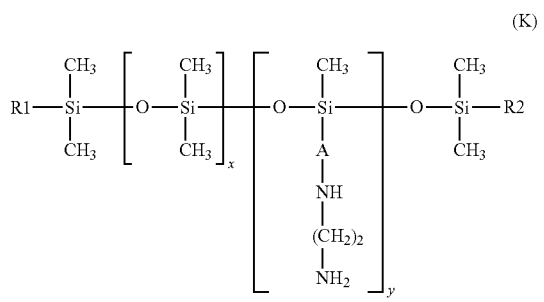

(K)

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms; and A denotes a linear or branched alkylene radical containing from 2 to 8 carbon atoms.

In various exemplary embodiments, A comprises from 3 to 6 carbon atoms, especially 4 carbon atoms, and in certain embodiments, A is branched. Mention may be made of the following divalent radicals: —$CH_2CH_2CH_2$— and —$CH_2CH(CH_3)CH_2$—.

Preferably, $R_1$ and R2, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and R2, which may be identical or different, are chosen from hexadecyl (cetyl) and octadecyl (stearyl) radicals.

In various exemplary embodiments, the silicone of formula (K) is chosen such that:

x ranges from 10 to 2000 and especially from 100 to 1000;

y ranges from 1 to 100;

A comprises 3 to 6 carbon atoms and especially 4 carbon atoms; preferably, A is branched; and more particularly A is chosen from the following divalent radicals: $CH_2CH_2CH_2$ and —$CH_2CH(CH_3)CH_2$—; and $R_1$ and R2, which may be identical or different, are linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

An exemplary amino silicone of formula (K) is bis-cetearylamodimethicone (INCI name), such as the silicone sold under the name SILSOFT AX by Momentive.

h) silicone compounds with at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. For example, quaternium 80, silicone quaternium-16, silicone quaternium-18, silicone quaternium-15, or mixtures thereof may be chosen.

The amount of the at least one silicone copolymer that may be included in various embodiments can vary but typically ranges from about 0.1% to about 10%, including all subranges therebetween, such as from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 0.5% to about 1%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 1.5% to about 10%, from about 1.5% to about 9%, from about 1.5% to about 8%, from about 1.5% to about 7%, from about 1.5% to about 6%, from about 1.5% to about 5%, from about 1.5% to about 4%, from about 1.5% to about 3%, from about 1.5% to about 2%, from about 2% to about 10%, from about 2% to about 9%, from about 2% to about 8%, from about 2% to about 7%, from about 2% to about 6%, from about 2% to about 5%, from about 2% to about 4%, or from about 2% to about 3% by weight, relative to the total weight of the composition.

Nonionic Emulsifiers

Compositions according to the disclosure comprise at least one nonionic emulsifier. Exemplary nonionic emulsifiers include:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula [$R^1R^2R^3N \rightarrow O$] where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula [RR'R"P$\rightarrow$O] where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), including APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside, which is commercially available from Henkel, ICI Americas, and Seppic; and (8) polyoxyethylene alkyl ethers such as those of the formula RO($CH_2CH_2O)_nH$ and polyethylene glycol (PEG) glyceryl fatty esters, such as those of the formula R(O)OCH$_2$CH(OH)CH$_2$(OCH$_2$CH$_2)_n$OH, wherein n is from 1 to about 200, preferably from about 20 to about 100, and R is an alkyl having from about 8 to about 22 carbon atoms.

Polyethylene glycol derivatives of glycerides as described in the above (8) useful herein include derivatives of mono-, di- and tri-glycerides and mixtures thereof. One class of polyethylene glycol derivatives of glycerides suitable herein is those which conform to the following general formula:

wherein:

n, the degree of ethoxylation, is from about 4 to about 200, preferably from about 5 to about 150, more preferably from about 20 to about 120, and R comprises an aliphatic radical having from about 5 to about 25 carbon atoms, preferably from about 7 to about 20 carbon atoms.

Suitable polyethylene glycol derivatives of glycerides can be polyethylene glycol derivatives of hydrogenated castor oil. Such polyethylene glycol derivatives of hydrogenated castor oil include, for example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil.

Other suitable polyethylene glycol derivatives of glycerides can be polyethylene glycol derivatives of stearic acid. Such polyethylene glycol derivatives of stearic acid include, for example, PEG-30 stearate, PEG-40 stearate, PEG-50 stearate, PEG-75 stearate, PEG-90 stearate, PEG-100 stearate, PEG-120 stearate, and PEG-150 stearate.

Ethylene glycol ethers of fatty alcohols, as described in the above (3) or (8), useful herein include any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, preferably ceteth-7 through ceteth-20; the isoceteth series of compounds such as isoceteth-20; the steareth series of compounds such as steareth-1 through 100; ceteareth 1 through ceteareth-50; the laureth series of compounds, preferably laureth-7 through Laureth-12; the pareth series of compounds, preferably pareth-9 through pareth-15; propylene glycol ethers of the above ceteth, steareth, ceteareth, and laureth series of compounds, such propylene glycol ethers of ceteth series of compounds including, for example, PPG-5-Ceteth-20; polyoxyethylene ethers or polyoxyethylene-polyoxypropylene ethers of branched alcohols, such branched alcohols including, for example, octyldodecyl alcohol, decyltetradecyl alcohol, dodecylpentadecyl alcohol, hexyldecyl alcohol, and isostearyl alcohol, and such polyoxyethylene-polyoxypropylene ethers of branched alcohols including, for example, POE(20)POP(6) decyltetradecyl ether; and mixtures thereof.

Still further useful nonionic emulsifiers include polysorbates, such as, for example, polysorbate-20 (POE(20) sorbitan monolaurate) having HLB value of 16.7, polysorbate-21 (POE(4) sorbitan monolaurate) having HLB value of 13.3, polysorbate-40 (POE(20) sorbitan monopalmitate) having HLB value of 15.6, polysorbate-60 (POE(20) sorbitan monostearate) having HLB value of 14.9, polysorbate-61 (POE(4) sorbitan monostearate) having HLB value of 9.6, polysorbate-80 (POE(20)sorbitan monooleate) having HLB value of 15.0, and polysorbate-81 (POE(4) sorbitan monooleate) having HLB value of 10.0.

In preferred embodiments, the at least one non-ionic emulsifier is a polysorbate. The polysorbate useful herein may be, for example, polysorbate-20, polysorbate-21, polysorbate-40, polysorbate-60, polysorbate-80, and mixtures thereof.

In various embodiments, the at least one nonionic emulsifier may be contained in a composition at a level by weight ranging from about 0.01% to about 5%, including all subranges therebetween, such as from about 0.05% to about 3%, from about 0.05% to about 2%, from about 0.05% to about 1%, from about 0.05% to about 0.5%, from about 0.1% to about 3%, from about 0.1% to about 2%, from about 0.1% to about 1%, from about 0.1% to about 0.5%, or from about 0.2% to about 0.4%, relative to the total weight of the composition.

In some embodiments, the compositions described herein may further comprise an additional cosmetic safe emulsifier other than the at least one non-ionic emulsifier, or co-emulsifier thereof. Such additional emulsifier may be a cationic emulsifier and/or an anionic emulsifier. Non-limiting examples of the additional emulsifier include glyceryl stearate, potassium cetyl sulfate, laureth sulfate, Ceteareth-20, etc.

Solvents

Compositions according to the disclosure comprise a solvent. The solvent may be chosen from water, non-aqueous solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises, consists essentially of, or consists of non-aqueous solvents, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. Non-limiting examples of solvents which may be used include alkanediols such as glycerin, 1,2,6-hexanetriol, trimethylolpropane, ethylene glycol, propylene glycol, butylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the solvent may be selected from the group consisting of one or more glycols, $C_{1-4}$ alcohols, glycerin, and a mixture thereof. For example, the solvent may be selected from the group consisting of hexylene glycol, proplene glycol, butylene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, butylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2, 6-hexanetriol, and a mixture thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The solvent may be present in the composition in an amount ranging from about 60% to about 98% by weight, relative to the total weight of the composition, including all ranges and subranges therebetween. For example, in one embodiment, the total amount of water may be about 75% to about 98%, about 75% to about 95%, about 75% to 93%, or about 75% to about 90% by weight, relative to the total weight of the composition.

Additional Components

Compositions according to the disclosure may optionally further comprise additional components useful for the hair treatment compositions described herein.

Fatty Compounds

Compositions according to the disclosure may optionally comprise at least one fatty compound. Non-limiting examples of fatty compounds include oils, mineral oil, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/ glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, undecane, tridecane, 2-oleamido-1,3-octadecanediol (ceramide), and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

As used herein, "fatty alcohol" refers to any alcohol with a carbon chain of C5 or greater, such as, for example, C8 or greater, C10 or greater, and C12 or greater. The fatty alcohols useful according to the disclosure include, but are not limited to, alkoxylated or non-alkoxylated, saturated or unsaturated, linear or branched, fatty alcohols, for example with from 6 to 30 carbon atoms, such as from 8 to 30 carbon atoms.

Fatty alcohol derivatives include alkyl ethers of fatty alcohols, alkoxylated fatty alcohols, alkyl ethers of alkoxylated fatty alcohols, esters of fatty alcohols and a mixture thereof. As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater.

Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG-8-ceteth-1, and PPG-10 cetyl ether; and mixtures of all of the foregoing compounds.

Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

Non-limiting polyglycerol esters of fatty acids include those of the following formula:

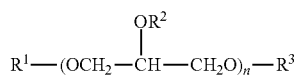

$$R^1-(OCH_2-CH(OR^2)-CH_2O)_n-R^3$$

wherein the average value of n is about 3 and R1, R2 and R3 each may independently be a fatty acid moiety or hydrogen, provided that at least one of R1, R2, and R3 is a fatty acid moiety. For instance, R1, R2 and R3 may be saturated or unsaturated, straight or branched, and have a length of C1-C40, C1-C30, C1-C25, or C1-C20, C1-C16, or C1-C10. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of a nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

According to various embodiments, the at least one fatty compound that can be included in the compositions disclosed herein may, in some embodiments, be chosen from liquid fatty alcohols. In some further embodiments, the at least one fatty compound may be chosen from solid fatty alcohols. In some embodiments, the at least one fatty compound may be chosen from combinations of at least one liquid fatty alcohol and at least one solid fatty alcohol.

According to various embodiments, liquid fatty alcohols are included in the compositions, in particular those containing C10-C34, may have branched carbon chains and/or have branched and/or unsaturated (C═C double bond), and contain from 12 to 40 carbon atoms. The liquid fatty alcohols may be represented by the formula R—OH, wherein R denotes a C12-C24 branched alkyl group or an alkenyl group (comprising at least one C12-C24 double bond C═C), R being optionally substituted by one or more hydroxy groups. In some embodiments, the liquid fatty alcohol is a branched saturated alcohol. In at least certain embodiments, R does not contain a hydroxyl group. The liquid fatty alcohol may be chosen from oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

According to further embodiments, solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm. The solid fatty alcohols may be soluble, under the same temperature and pressure conditions, in at least one organic solvent (for example ethanol, chloroform, benzene or liquid petroleum jelly) to at least 1% by weight.

The solid fatty alcohols may be represented by the formula R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The solid fatty alcohols may include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol); or mixtures thereof. In some embodiments, the compositions disclosed herein comprise at least one solid fatty alcohol chosen from cetyl alcohol, stearyl alcohol, behenyl alcohol and mixtures thereof such as cetylstearyl or cetearyl alcohol.

Thus, without intending to be limiting, the at least one fatty compound may be chosen from C9-C11 alcohols, C12-C13 alcohols, C12-C15 alcohols, C12-C16 alcohols, C14-C15 alcohols, C12-C22 alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, tridecyl alcohol, 2-octyldodecanol, isostearyl alcohol, 2-hexyldecanol, 2-heptyldecanol, 2-octyldecanol, caproic alcohol (1-hexanol), enanthic alcohol (1-heptanol), caprylic alcohol (1-octanol), pelargonic alcohol (1-nonanol), capric alcohol (1-decanol), lauryl alcohol (1-dodecanol), or a mixture thereof. For example, in one embodiment, the at least one fatty alcohol is octyldodecanol. In one embodiment, the at least one fatty alcohol is cetyl alcohol. In one embodiment, the at least one fatty alcohol is cetearyl alcohol. In one embodiment, the at least one fatty alcohol comprises both cetyl alcohol and cetearyl alcohol By way of example, ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceterael:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetyl-steareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, C22-C24 pareth-33, or a mixture thereof may be chosen.

When at least one fatty compound is included in a composition disclosed herein, the total amount of the at least one fatty compound, in various embodiments, may range up to about 10% by weight, relative to the total weight of the composition. For instance, in some cases, the total amount of the at least one fatty compound may be about 0.01% up to about 10% by weight, about 0.01% to about 5%, about 0.1% to about 10%, about 0.1% to about 5%, about 1% to about 10%, or about 1% to about 5% by weight, based on the weight of the composition.

Cationic Conditioning Agents

Compositions according to the disclosure may further optionally comprise at least one cationic conditioning agent.

In some embodiments, the at least one cationic conditioning agent may be chosen from amidoamine compounds (or amidoamines). Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and mixtures thereof.

In some further embodiments, cationic conditioning agents can be chosen from monoalkyl quaternary amines, dialkyl quaternary amines, or polyquaternium compounds or salts thereof.

For example, cationic conditioning agents may be chosen from Polyquaterium-(also called quaternized polyhydroxyethyl cellulose), cetrimonium chloride, behentrimonium chloride, behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Polyquaternium-37 (e.g., under the SALCARE tradename), Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

In various embodiments, cationic polymers that may be chosen include, but are not limited to: polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, or guar hydroxypropyltrimonium chloride, and mixtures thereof. In an embodiment, the cationic conditioning agent is chosen from Polyquaternium-67, Polyquaternium-10, Polyquaternium-37, or mixtures thereof. Polyquaternium-37 may be commercially available from BASF under the tradename of SALCARE SC 96 (comprising Polyquaternium-37 (and) Propylene Glycol Dicaprylate/Dicaprate (and) PPG-1 Trideceth-6).

When the at least one cationic conditioning agent is included in a composition described herein, the total amount of the at least one cationic conditioning agent may range up to about 10% by weight, related to the total weight of the composition. For instance, in some cases, the total amount of the at least one cationic conditioning agent may be about 0.01% to about 10%, about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, about 0.01% to about 1%, about 0.1% to about 10%, about 0.1% to about 9%, about 0.1% to about 8%, about 0.1% to about 7%, about 0.1% to about 5%, about 0.1% to about 5%, about 0.1% to about 4%, about 0.1% to about 3%, about 0.1% to about 2%, or about 0.1% to about 1% by weight, relative to the total weight of the composition.

Cationic Surfactants

In various embodiments, compositions according to the disclosure may optionally comprise at least one cationic surfactant. The term "cationic surfactant" means a surfactant comprising, as ionic or ionizable groups, only cationic groups. It is understood that cationic surfactants, if present, may be included in addition to cationic conditioning agents. Non-limiting examples of cationic surfactants that may be used include polyoxyalkylenated primary, secondary, or tertiary fatty amine salts, quaternary ammonium salts, and mixtures thereof.

As quaternary ammonium salts, quaternary ammonium salts of formula (V) may be chosen:

wherein:

groups R8 to R11 are independently chosen from linear or branched aliphatic groups containing from 1 to 30 carbon atoms, or an aromatic group such as aryl or alkylaryl, at least one of the groups R8 to R11 including from 8 to 30 carbon atoms, such as from 12 to 24 carbon atoms, it being possible for the linear or branched aliphatic groups to include heteroatoms such as, for example, oxygen, nitrogen, and/or sulfur, these heteroatoms not being adjacent, and halogens; and $X^-$ is an anion chosen from the group consisting of halides such as bromides, chlorides, iodides, fluorides, phosphates, acetates, lactates, (C1-C4)alkyl sulfates, (C1-C4)alkyl sulfonates or (C1-C4)alkylaryl sulfonates; C1-C30 alkyl, C1-C30 alkoxy, (C2-C6)polyoxyalkylene, C1-C30 alkylamide, (C12-C22)alkyl-(C2C6)alkylamido, (C12-C22)alkyl acetate, and C1-C30 hydroxyalkyl groups.

Mention may be made as exemplary embodiments of formula (V) of tetraalkylammonium halides, such as chlorides, for example dialkyldimethylammonium or alkyltrimethylammonium chlorides in which the alkyl group comprises from 12 to 22 carbon atoms, such as from 14 to 20 carbon atoms. By way of example, behenyltrimethylammonium chloride (behentrimonium chloride), distearyl-dimethylammonium chloride, cetyltrimethylammonium chloride (cetrimonium chloride), or benzyldimethylstearylammonium chloride may be chosen.

Mention may also be made of palmitylamidopropyltrimethylammonium or stearamidopropyldimethyl-(myristyl acetate)-ammonium halides, such as chlorides, for example the product sold under the name Ceraphyl® 70 by the company Van Dyk.

In certain embodiments, cationic surfactants of formula (V) are preferably chosen from alkyltrimethylammonium halides whose alkyl group includes from 12 to 22 carbon atoms, such as from 14 to 20 carbon atoms, may be chosen. For example, alkyltrimethylammonium chlorides, such as behenyltrimethylammonium chloride and cetyltrimethylammonium chloride, may be particularly useful.

In further embodiments, quaternary ammonium salts of imidazoline of formula (VI) may be chosen:

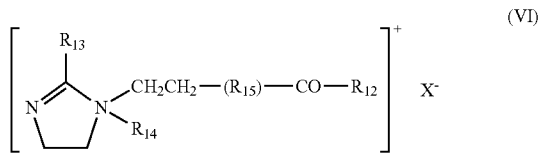

wherein:
$R_{12}$ represents an alkenyl or alkyl group comprising from 8 to 30 carbon atoms, for example derived from tallow fatty acids,
$R_{13}$ represents a hydrogen atom, a C1-C4 alkyl group or an alkenyl or alkyl group comprising from 8 to 30 carbon atoms,
$R_{14}$ represents a C1-C4 alkyl group,
$R_{15}$ represents a hydrogen atom or a C1-C4 alkyl group, and
$X^-$ is an anion chosen from the group consisting of halides, phosphates, acetates, lactates, (C1-C4)alkyl sulfates, and (C1-C4)alkyl- or (C1-C4)alkylarylsulfonates.

In one exemplary embodiment of formula (VI), $R_{12}$ and $R_{13}$ denote a mixture of alkenyl or alkyl groups comprising from 12 to 21 carbon atoms, for example derived from tallow fatty acids, $R_{14}$ denotes a methyl group, and $R_{15}$ denotes a hydrogen atom. Such a product is sold, for example, under the name Rewoquat® W75 or W90 by the company Evonik.

In yet further embodiments, di- or triquaternary ammonium salts of formula (VII) may be chosen:

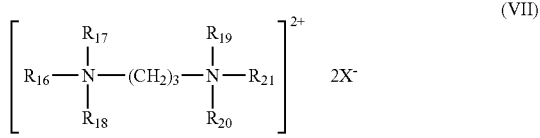

wherein:
$R_{16}$ represents an alkyl group comprising from 16 to 30 carbon atoms, which is optionally hydroxylated and/or optionally interrupted with one or more oxygen atoms,
$R_{17}$ represents hydrogen, an alkyl group comprising from 1 to 4 carbon atoms, or a group —(CH2)3—N$^+$(R16a)(R17a)(R18a),
R16a, R17a and R18a, which may be identical or different, represent hydrogen or an alkyl group comprising from 1 to 4 carbon atoms, $R_{18}$, $R_{19}$, $R_{20}$, and $R_{21}$, which may be identical or different, represent hydrogen or an alkyl group comprising from 1 to 4 carbon atoms, and
$X^-$ is an anion chosen from the group consisting of halides, acetates, phosphates, nitrates, (C1-C4)alkyl sulfates, and (C1-C4)alkyl- and (C1-C4)alkylarylsulfonates, for example methyl sulfate or ethyl sulfate.

Such compounds are, for example, Finquat CT-P (Quaternium 89) and Finquat CT (Quaternium 75), sold by the company Finetex.

In still further embodiments, quaternary ammonium salts containing one or more ester functions, such as those of formula (VIII) may be chosen:

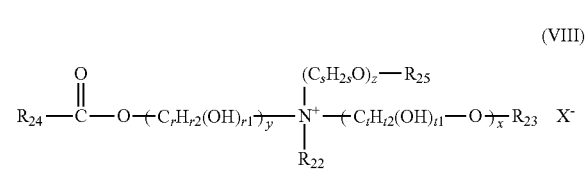

wherein:
$R_{22}$ is chosen from C1-C6 alkyl groups and C1-C6 hydroxyalkyl or dihydroxyalkyl groups,
$R_{23}$ is chosen from the group R26—C(=O)—; linear or branched, saturated or unsaturated C1-C22 hydrocarbon-based groups; and a hydrogen atom,
$R_{25}$ is chosen from the group R28—C(=O)—; linear or branched, saturated or unsaturated C1-C6 hydrocarbon-based groups; and a hydrogen atom,
$R_{24}$, $R_{26}$, and $R_{28}$, which may be identical or different, are chosen from saturated or unsaturated, linear or branched C7-C21 hydrocarbon-based groups,
r, s and t, which may be identical or different, are integers ranging from 2 to 6,
r1 and t1, which may be identical or different, are equal to 0 or 1,
y is an integer ranging from 1 to 10,
x and z, which may be identical or different, are integers ranging from 0 to 10, and
$X^-$ is an anion,
it being understood that r2+r1=2r and t1+t2=2t, and that the sum x+y+z ranges from 1 to 15, with the proviso that when x=0 then R23 is chosen from C1-C22 hydrocarbon-based groups, and that when z=0 then R25 denotes a linear or branched, saturated or unsaturated C1-C6 hydrocarbon-based group.

In exemplary embodiments of formula (VIII), the alkyl groups $R_{22}$ may be linear or branched, and are preferably linear. Preferably, $R_{22}$ denotes a methyl, ethyl, hydroxyethyl or dihydroxypropyl group, and more particularly a methyl or ethyl group. Advantageously, the sum x+y+z ranges from 1 to 10. When R23 is a C1-C22 hydrocarbon-based groups, it may preferably comprise either from 12 to 22 carbon atoms or from 1 to 3 carbon atoms. Advantageously, R24, R26 and R28, which may be identical or different, are chosen from linear or branched, saturated or unsaturated C11-C21 hydrocarbon-based groups, and more particularly from linear or branched C11-C21 alkyl and alkenyl groups. Preferably, x and z, which may be identical or different, are equal to 0 or 1. Optionally, y is equal to 1. Preferably, r, s, and t, which may be identical or different, are equal to 2 or 3, and optionally are equal to 2.

The anion $X^-$ is preferably a halide, optionally chloride, bromide, or iodide, a (C1-C4)alkyl sulfate, a (C1-C4)alkylsulfonate, or a (C1-C4)alkylarylsulfonate, a methanesulfonate, a phosphate, a nitrate, a tosylate, an anion derived from an organic acid such as an acetate or a lactate, or any other anion that is compatible with the ammonium bearing an ester function. The anion X– is more particularly a chloride, a methyl sulfate, or an ethyl sulfate.

For example, the ammonium salts of formula (VIII) in which R22 denotes a methyl or ethyl group, x and y are equal to 1, z is equal to 0 or 1, r, s and t are equal to 2, R23 is chosen from the group R26—C(=O)—, methyl, ethyl, or C14-C22 hydrocarbon-based groups; and a hydrogen atom, R25 is chosen from the group R28-C(=O)—; and a hydrogen atom, R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups, may be chosen. Advantageously, the hydrocarbon-based groups are linear.

Among the compounds having formula (VIII), mention may be made of salts, especially the chloride or methyl sulfate salts, of diacyloxyethyldimethylammonium, diacyloxyethylhydroxyethylmethylammonium, monoacyloxyethyldihydroxyethylmethyl-ammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures especially of plant or animal origin, or by transesterification of the methyl esters thereof. This esterification may be followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are sold, for example, under the names Dehyquart® by the company Henkel, Stepanquat® by the company Stepan, Noxamium® by the company CECA or Rewoquat® WE 18 by the company Evonik.

The one or more cationic surfactants may be chosen from, for example, a mixture of quaternary ammonium monoester, diester and triester salts with a weight majority of diester salts. Use may also be made of the ammonium salts containing at least one ester functional group that are described in patents U.S. Pat. Nos. 4,874,554 and 4,137,180. Use may also be made of behenoylhydroxypropyl-trimethylammonium chloride, for example, sold by the company Kao under the name Quartamin BTC 131. Preferably, the ammonium salts containing at least one ester function contain two ester functions.

When one or more cationic surfactants are included in the compositions, the total amount of the one or more cationic surfactants may range up to about 15%, based on the total weight of the composition, including all ranges and subranges therebetween. For instance, the total amount of the one or more cationic surfactants may range from about 0.1% to about 15%, from about 0.1% to about 10%, from about 0.1% to about 5%, from about 0.1% to about 3%, from about 0.5% to about 15%, from about 0.5% to about 10%, from about 0.5% to about 5%, from about 0.5% to about 3%, from about 1% to about 15%, from about 1% to about 10%, from about 1% to about 5%, from about 1% to about 3%, by weight, relative to the total weight of the hair treatment composition.

Active Agents

In various embodiments, compositions according to the disclosure may optionally comprise at least one active agent such as an acid or sodium hydroxide, or mixture thereof, to provide optimized strengthening benefits to the hair. Non-limiting examples of useful acids include glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, or mixtures thereof.

The acids are typically non-polymeric and may have one (mono), two (di), or three (tri) carboxylic acid groups (—COOH). The non-polymeric mono-, di-, and tricarboxylic acids, and/or salts thereof, typically have a molecular weight of less than about 500 g/mol, less than about 400 g/mol, or less than about 300 g/mol.

Non-limiting examples of monocarboxylic acids include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof.

Non-limiting examples of dicarboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof.

Non-limiting examples of tricarboxylic acids include citric acid, isocitric acid, aconitric acid, propane-1,2,3-tricarboxylic acid, benzene-1,3,5-tricarboxylic acid, a salt thereof, and a mixture thereof.

If present, the total amount of the one or more acids may vary but typically ranges from about 0.0001% to about 10%, such as from about 0.0001% to about 5%, about 0.0001% to about 1%, about 0.001% to about 10%, about 0.001% to about 5%, about 0.001% to about 1% by weight, about 0.01% to about 10%, about 0.01% to about 5%, about 0.01% to about 1%, about 0.1% to about 10%, about 0.1% to about 5%, or about 0.1% to about 1% by weight, based on the total weight of the composition. For example, the total amount of the one or more acids may range from about 0.0001% to about 0.5% by weight, based on the total weight of the composition.

Thickening Agents (Thickeners)

The compositions further may optionally contain one or more thickeners (also referred to as thickening agents or viscosity modifying agents). Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions.

The total amount of the one or more thickening agents may vary, but in some cases ranges from about 0.1% to about 15%, from about 0.1% to about 10%, from about 0.1% to about 5%, from about 0.1% to about 2%, from about 0.5% to about 20%, from about 0.5% to about 15%, from about 0.5% to about 10%, from about 0.5% to about 5%, from about 1% to about 20%, from about 1% to about 15%, from about 1% to about 10%, from about 1% to about 5%, from about 2% to about 20%, from about 2% to about 15%, from about 2% to about 10%, relative to the total weight of the composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. In some cases, the hair-treatment compositions may include one or more preservatives selected from the group consisting of sodium benzoate, benzoic acid, chlorhexidine digluconate, chlorhexidine dihydrochloride, salicylic acid, phenoxyethanol, methyl paraben, and a mixture thereof.

The total amount of the one or more preservatives, when present, may vary. In some cases, the total amount of the one or more preservatives is about 0.01% to about 5%, about 0.01% to about 4%, about 0.15% to about 1%, or about 1% to about 3%, by weight, relative to the total weight of the composition.

Auxiliary Components

Compositions according to the disclosure may be in any suitable form, preferably an emulsion. Thus, compositions according to the disclosure may optionally comprise any auxiliary component suitable for use in cosmetic compositions such as emulsions. Such components may include, but are not limited to, dyes/pigments, film forming agents or polymers, humectants and moisturizing agents, fatty substances other than fatty alcohols, fillers, structuring agents, propellants, shine agents, antioxidants or reducing agents, penetrants, sequestrants, fragrances, buffers, dispersants, plant extracts, preserving agents, opacifiers, sunscreen agents, vitamins, pH adjusting agents, and antistatic agents.

Optional auxiliary components may be present in an amount ranging up to about 15% by weight, relative to the total weight of the composition.

II. Packaging Systems and Kits

The disclosure also relates to packaging systems and kits comprising the composition.

Packaging Systems

The packaging systems comprise at least one container suitable for containing and/or applying the composition. The container may be prefilled with a composition according to the disclosure, or may be filled by the user at or near the time of use. The container may be any size or shape, and may be made of any suitable material(s).

In various embodiments, the container may be single-use, e.g. contain an amount of composition suitable for one application, or may be multiple-use, e.g. contain an amount of composition suitable for multiple applications. For example, the container may be a single-use ampoule, packet, pouch, or syringe containing an amount of composition suitable for a single application, or may be a multiple-use syringe, squeeze tube or bottle, packet, or pouch containing an amount of composition suitable for multiple applications.

The container has an opening configured for dispensing the composition contained therein. In some embodiments, the container has graduated marks or lines indicating the volume of the composition contained in the container. In some embodiments, the container is configured to be reusable and allows for refilling the composition therein. In some embodiments, the container is configured to be disposable, and does not allow refilling of the composition.

By way of non-limiting example, the container may be a syringe, with the understanding that syringes useful according to the disclosure typically do not comprise a needle. In an exemplary embodiment where the syringe contains an amount of composition suitable for multiple applications, it may have graduated marks or lines indicating the total volume of composition in the syringe and/or an amount the composition to be dispensed for each application, e.g. such that a user can dispense an effective or standardized amount or dose of a composition from the syringe each time at use. As such, an appropriate amount of the composition to be dispensed for applying to keratin fibers can be easily determined according to the volume measured by the graduated marks or lines. Packaging systems in the form of a syringe may be particularly useful to ensure an optimal amount of composition is applied to the keratin fibers with each treatment.

As further non-limiting examples, the container may be a tube, a jar, a bottle, packet, pouch, etc. For example, the container may be a squeeze tube or squeeze bottle that may optionally have graduated marks or lines indicating the total volume of composition in the tube or bottle and/or an amount the composition to be dispensed for each application, such that a user can dispense an effective or standardized amount or dose of a composition from the squeeze tube or squeeze bottle each time at use. As such, effective amount of the composition to be dispensed for applying to keratin fibers can be easily determined according to the volume measured by the graduated marks or lines.

Kits

Kits according to the disclosure may comprise packaging systems disclosed herein. For example, a kit may comprise a first container containing a composition disclosed herein. Optionally, kits according to the disclosure may comprise a second container. For example, a kit may optionally further comprise a second container comprising a hair composition other than the compositions disclosed herein, including but not limited to a hair-treatment rinse, a shampoo, a hair-color-toning composition, a hair lightening composition, a hair coloring composition, a hair relaxing composition, a hair straightening composition, a hair waving composition, or a skin care or make-up composition.

In further exemplary embodiments, the kits may contain at least one first container containing a composition according to the disclosure and at least one second container configured to dispense or apply the compositions described herein. Thus, in one embodiment, a first container may be a jar or a bottle containing a composition according to the disclosure, and a second container may be a squeezable tube or bottle or a syringe, configured to be filled with the composition in order to apply the composition to the keratin fibers to be treated.

Container(s) configured to dispense or apply the compositions may, in various embodiments, be disposable or refillable.

III. Methods

Methods according to the disclosure comprise treating, caring for, or conditioning keratin fibers with the compositions described herein. The methods generally comprise applying any of the disclosed compositions to the keratin fibers, and optionally subsequently rinsing the compositions.

When using the compositions as a rinse-off composition, the composition may be allowed to remain on the keratin fiber for any desired amount of time, for example from about a few seconds (e.g. about 5, 10, 20, or 30 seconds) to about 1, 2, 3, 5, 10, 20, or 30 minutes, or longer.

Alternatively, when the hair-treatment composition is a leave-in product, the methods may include applying a sufficient amount of the leave-in product to hair (either wet, damp, or dry hair), and optionally, drying and/or styling the hair. The composition may be left on the hair for any period of time, such as a few hours or a few days, or until the next washing or rinsing of the hair.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated. It is to be understood that all definitions herein are provided for the present disclosure only.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the compositions.

In this application, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations. Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

Throughout the disclosure, if the term "a mixture thereof," including variants, is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

"Active material" as used herein with respect to the percent amount of an ingredient or raw material, refers to 100% activity of the ingredient or raw material. All amounts given herein are relative to the amount of active material, unless otherwise indicated. Thus, for example, "about 1% to about 3% of at least one silicone copolymer" means that although the amount of silicone copolymer added to the formulation ranges from about 1% to about 3%, the total amount of a commercial product comprising the silicone copolymer that is added to the formulation may be greater (e.g. may be from about 2% to about 6% if the product is 50% active material).

As used herein, the terms "applying a composition onto keratin fibers" and "applying a composition onto hair" and variations of these phrases are intended to mean contacting the keratin fibers or hair, with at least one of the compositions of the invention, in any manner. It may also mean contacting the keratin fibers or hair in an effective amount Unless otherwise indicated, all percentages herein are by weight, relative to the weight of the total composition.

As used herein, the term "conditioning" means imparting to hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work, and consumer perception.

As used herein, "cosmetic composition" encompasses many types of compositions for application to keratin fibers such as hair, for example, hair lotions, hair creams, hair gel creams, hair conditioners, hair masques (masks), etc., which can be used either as leave-on or rinse-off treatments or products.

As used herein, the term "salts" refers to throughout the disclosure may include salts having a counter-ion such as an alkali metal, alkaline earth metal, or ammonium counterion. This list of counterions, however, is non-limiting.

A "rinse-off" product refers to a composition such as a hair-treatment composition that is rinsed and/or washed with water either after or during the application of the composition onto the keratin fiber, and before drying and/or styling said keratin fiber. At least a portion, and typically most, of the composition is removed from the keratin fibers during the rinsing and/or washing.

A "leave-on" product refers to a composition such as a hair-treatment composition that is not rinsed and/or washed with water or acceptable solvent after the application of the composition onto the keratin fiber; instead, the composition is allowed to remain on the fibers for a period of time, such from 1 hour, 2 hours, 3 hours, 4 hours, up to 8 hours, or overnight.

As used herein, the term "stable" indicates that the composition does not exhibit phase separation and/or crystallization for a period of time, for example, for at least 1 day (24 hours), one week, one month, or one year.

The terms "substantially free" or "essentially free" as used herein means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

As used herein, the term "surfactants" includes salts of the surfactants even if not explicitly stated.

As used herein, the term "synthetic" means a material that is not of natural origin. The term "natural" means a material of natural origin, such as derived from plants, which also cannot be subsequently chemically or physically modified.

As used herein, the term "treat" (and its grammatical variations) refers to the application of the compositions of the present disclosure onto the keratin fibers.

As used herein, the term "volatile" means having a flash point of less than about 100° C.

As used herein, the term "non-volatile" means having a flash point of greater than about 100° C.

EXAMPLES

The following examples are intended to be non-limiting and explanatory in nature only. In the Examples, amounts are expressed in percentage by weight (wt %) of active materials.

Example 1—Hair Treatment Compositions

The following inventive and comparative compositions were prepared according to the formulations set forth in Table 1 below.

TABLE 1

| INCI Name | Inventive Compositions | | Comparative Compositions | | | | | |
|---|---|---|---|---|---|---|---|---|
| | I1 | I2 | C1 | C2 | C3 | C4 | C5 | C6 |
| ARGININE | 2.0 | 2.0 | 0.06 | 2.0 | 2.0 | 2.0 | 2.0 | 2.0 |
| GLUTAMIC ACID | 2.0 | 2.0 | — | 2.0 | 2.0 | 2.0 | 2.0 | 2.0 |
| PEG-40/PPG-8 METHYLAMINOPROPYL/ HYDROXYPROPYL DIMETHICONE COPOLYMER | 1.5 | 1.5 | 1.2 | 1.2 | 1.425 | 1.5 | 1.56 | 1.5 |
| POLYSORBATE 20 | 0.25 | 0.25 | — | — | — | — | — | — |
| SORBITAN OLEATE | — | 0.05 | — | — | — | — | — | — |
| CETYL ALCOHOL | 0.12 | 0.12 | 0.12 | 0.12 | 0.12 | 0.12 | 0.12 | 0.12 |
| BEHENTRIMONIUM METHOSULFATE | 0.048 | 0.048 | 0.048 | 0.048 | 0.048 | 0.048 | 0.048 | 0.048 |
| QUATERNIUM-33 | 0.032 | 0.032 | 0.032 | 0.032 | 0.032 | 0.032 | 0.032 | 0.032 |
| BEHENTRIMONIUM CHLORIDE | 4.74 | 4.4 | 3.16 | 4.74 | 4.74 | 4.74 | 4.74 | 4.74 |
| HYDROLYZED VEGETABLE PROTEIN | 0.145 | 0.145 | 0.145 | — | — | — | — | 0.145 |
| POLY-QUATERNIUM-67 | 0.4 | — | 0.25 | 0.25 | 0.35 | 0.4 | 0.4 | 0.4 |
| POLY-QUATERNIUM-37 (and) PROPYLENE GLYCOL DICAPRYLATE/ DICAPRATE (and) PPG-1 TRIDECETH-6 | — | 2.33 | — | — | — | — | — | — |
| POLY-QUATERNIUM-10 | — | 0.4 | — | — | — | — | — | — |
| TRIDECETH-6 | — | 0.2 | — | — | — | — | — | — |
| AMODIMETHICONE | — | 2.3 | — | — | — | — | — | — |
| CETRIMONIUM CHLORIDE | — | 0.04 | — | — | — | — | — | — |
| CETEARYL ALCOHOL | 4 | 4 | 3.5 | 6 | 4 | 4.0 | 4.0 | 4.0 |
| CITRIC ACID | 0.80 | 0.80 | 0.085 | 0.55 | 0.80 | 0.80 | 0.80 | 0.80 |
| CREATINE | — | — | 0.10 | — | — | — | — | — |
| CERAMIDE | — | — | 0.01 | — | — | — | — | — |

TABLE 1-continued

| INCI Name | Inventive Compositions | | Comparative Compositions | | | | | |
|---|---|---|---|---|---|---|---|---|
| | I1 | I2 | C1 | C2 | C3 | C4 | C5 | C6 |
| ADDITIVES (fragrance, preservatives, thickeners) | 1.46 | 1.0 | 1.46 | 1.40 | 1.40 | 1.40 | 1.40 | 1.46 |
| SOLVENT (water + non-aqueous solvents) | QS | QS | QS | QS | QS | QS | QS | QS |

Each of compositions I1-I2 and C1-C6 was prepared by mixing solvents, cationic polymers, and thickeners, and heating the mixture to 70° C. The fatty alcohols and surfactants were added and the mixture was homogenized for 10 minutes before the mixture was cooled. Once the mixture reached 45° C., the remaining ingredients were added and homogenized for 5 minutes, and then the composition was cooled to room temperature.

A visual evaluation of compositions I1-I2 and C1-C6 revealed that compositions according to the disclosure had better stability than compositions C1-C6. For example, composition C6 showed phase separation at elevated temperatures, whereas composition I1 did not.

Example 2—Evaluation of Properties and Performance

A comparative study was conducted to evaluate the properties and performance of inventive composition I1 in comparison with comparative compositions C2-C6 of Table 1. In this study, the hair of 13 different models was washed and rinsed, and an appropriate amount of one of compositions I1 or C2-C6 was respectively applied. After 5 minutes, the hair was rinsed and dried. The properties of the dried hair were evaluated, the results of which are summarized in Table 2.

TABLE 2

| | Performance properties/attributes | | | | |
|---|---|---|---|---|---|
| Formulation | Frizz Control | End Seal | Flexibility | Smoothing | Strong/ Healthy Hair Feel |
| I1 | ✓ | ✓ | ✓ | ✓ | ✓ |
| C2 | x | x | x | x | ✓ |
| C3 | x | x | ✓ | x | ✓ |
| C4 | ✓ | x | x | ✓ | ✓ |
| C5 | ✓ | x | x | x | x |
| C6 | ✓ | ✓ | ✓ | ✓ | ✓ |

In Table 2, where properties or attributes were observed, a "✓" is present, and where properties or attributes were not observed, an "x" is present. As can be seen, when compared to the comparative compositions, the treatment composition according to the disclosure (I1) delivered overall better performance and application properties to the hair than compositions C2-C5, providing hair with improved frizz control, good end seals, and sensorial properties such as silkier/smoothing touch from root to tip and compact feel.

In addition, inventive I1 provided strengthening benefit to hair as demonstrated by high tensile strength in cyclic fatigue test, compared with untreated hair.

Based on Examples 1 and 2 above, it was demonstrated that from a stability and benefits/properties point, compositions according to the disclosure provide surprising improvements relative to compositions not within the disclosure.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

The invention claimed is:

1. A composition for treating or caring keratin fibers comprising:
   (a) at least one negatively charged amino acid or a derivative thereof in an amount of at least about 1% by weight;
   (b) at least one positively charged amino acid or a derivative thereof in an amount of at least about 1% by weight;
   (c) at least one silicone copolymer; and
   (d) at least one nonionic emulsifier;
   wherein all amounts are relative to the total weight of the composition;
   wherein the weight ratio of the negatively charged amino acids or derivatives thereof to the positively charged amino acids or derivatives thereof is about 1:1; and
   wherein the composition is in the form of an emulsion.

2. The composition of claim 1, wherein:
   the at least one negatively charged amino acid or derivative thereof is chosen from glutamic acid, aspartic acid, derivatives thereof, or mixtures thereof; and
   the at least one positively charged amino acid or derivative thereof is chosen from arginine, lysine, histidine, ornithine, derivatives thereof, or mixtures thereof.

3. The composition of claim 1, wherein:
   the at least one negatively charged amino acid or derivative thereof is present in an amount ranging from about 2% to about 10% by weight, relative to the total weight of the composition; and
   the at least one positively charged amino acid or derivative thereof is present in an amount ranging from about 2% to about 10% by weight, relative to the total weight of the composition.

4. The composition of claim 1, wherein the at least one silicone copolymer is chosen from dimethicone, dimethicone copolymers, amino functional silicones, or mixtures thereof.

5. The composition of claim 1, wherein the at least one silicone copolymer is present in an amount ranging from about 0.1% to about 10% by weight, relative to the total weight of the composition.

6. The composition of claim 1, wherein the at least one nonionic emulsifier is chosen from polysorbates.

7. The composition of claim 1, wherein the at least one nonionic emulsifier is present in an amount ranging from about 0.01% to about 5% by weight, relative to the total weight of the composition.

8. The composition of claim 1, further comprising at least one conditioning agent.

9. The composition of claim 8, wherein the at least one conditioning agent is present in an amount ranging from about 0.01% to about 15% by weight, based on the total weight of the composition.

10. The composition of claim 1, further comprising at least one fatty compound.

11. The composition of claim 10, wherein the at least one fatty compound is chosen from fatty alcohols, fatty acids, fatty alcohol derivatives, fatty acid derivatives, or mixtures thereof.

12. A method of treating or caring for keratin fibers, comprising:
(1) applying to the keratin fibers a composition comprising:
(a) at least one negatively charged amino acid or a derivative thereof in an amount of at least about 1% by weight;
(b) at least one positively charged amino acid or a derivative thereof in an amount of at least about 1% by weight;
(c) at least one silicone copolymer; and
(d) at least one nonionic emulsifier;
wherein all amounts are relative to the total weight of the composition;
wherein the weight ratio of the negatively charged amino acids or derivatives thereof to the positively charged amino acids or derivatives thereof is about 1:1;
and
(2) optionally rinsing the composition from the keratin fibers.

13. The method of claim 12, wherein:
the at least one negatively charged amino acid or derivative is chosen from glutamic acid, aspartic acid, derivatives thereof, or mixtures thereof;
the at least one positively charged amino acid or derivative is chosen from arginine, lysine, histidine, ornithine, derivatives thereof, or mixtures thereof;
the at least one silicone copolymer is chosen from dimethicone, dimethicone copolymers, amino functional silicones, or mixtures thereof; and
the at least one nonionic emulsifier is chosen from polysorbates.

14. A packaging system comprising a container containing a composition for treating keratin fibers, the composition being in the form of an emulsion and comprising:
(a) at least one negatively charged amino acid or a derivative thereof in an amount of at least about 1% by weight;
(b) at least one positively charged amino acid or a derivative thereof in an amount of at least about 1% by weight;
(c) at least one silicone copolymer; and
(d) at least one nonionic emulsifier;
wherein all amounts are relative to the total weight of the composition; and
wherein the weight ratio of the negatively charged amino acids or derivatives thereof to the positively charged amino acids or derivatives thereof is about 1:1.

15. The packaging system of claim 14, wherein the container is chosen from an ampoule, a syringe, a tube, a packet, a pouch, or a bottle.

16. A kit comprising:
a first container comprising a first composition for treating keratin fibers, the first composition being in the form of an emulsion and comprising:
(a) at least one negatively charged amino acid or a derivative thereof in an amount of at least about 1% by weight;
(b) at least one positively charged amino acid or a derivative thereof in an amount of at least about 1% by weight;
(c) at least one silicone copolymer; and
(d) at least one nonionic emulsifier;
wherein all amounts are relative to the total weight of the composition; and
wherein the weight ratio of the negatively charged amino acids or derivatives thereof to the positively charged amino acids or derivatives thereof is about 1:1.

17. The kit of claim 16, wherein the first container is chosen from an ampoule, a syringe, a tube, a packet, a pouch, or a bottle.

18. The kit of claim 16, further comprising a second container configured to apply the composition to keratin fibers.

* * * * *